(12) United States Patent
Cudworth

(10) Patent No.: US 8,523,804 B2
(45) Date of Patent: Sep. 3, 2013

(54) BREAST ATTACHMENT

(75) Inventor: Nicholas Cudworth, Pittington (GB)

(73) Assignee: Jackel International Limited, Cramlington, Northumberland (GB)

( * ) Notice: Subject to any disclaimer, the term of this patent is extended or adjusted under 35 U.S.C. 154(b) by 0 days.

(21) Appl. No.: 13/383,773

(22) PCT Filed: Jul. 14, 2010

(86) PCT No.: PCT/GB2010/001345
§ 371 (c)(1),
(2), (4) Date: Feb. 28, 2012

(87) PCT Pub. No.: WO2011/007140
PCT Pub. Date: Jan. 20, 2011

(65) Prior Publication Data
US 2012/0165729 A1  Jun. 28, 2012

(30) Foreign Application Priority Data

Jul. 14, 2009  (GB) .................................. 0912229.2

(51) Int. Cl.
*A61M 1/06* (2006.01)
(52) U.S. Cl.
USPC .............................. 604/74; 604/313; 604/346
(58) Field of Classification Search
CPC ...................................................... A61M 1/06
USPC ......................................... 604/74, 313, 346
See application file for complete search history.

(56) References Cited

U.S. PATENT DOCUMENTS

| | | | |
|---|---|---|---|
| 1,690,327 A | 11/1928 | Dinesen | |
| 1,898,652 A | 2/1933 | Williams | |
| 2,364,866 A | 12/1944 | Meynier, Jr. | |
| 2,495,307 A * | 1/1950 | Abramson | .................... 128/890 |
| 3,343,422 A | 9/1967 | McSmith | |
| 1,161,118 A | 8/1969 | Einstein | |
| 4,249,481 A | 2/1981 | Adams | |
| 4,263,912 A | 4/1981 | Adams | |
| 4,323,067 A | 4/1982 | Adams | |
| 4,573,969 A | 3/1986 | Schlensog et al. | |
| 4,634,430 A | 1/1987 | Polaschegg | |
| 4,772,262 A | 9/1988 | Grant et al. | |
| 4,794,915 A | 1/1989 | Larsson | |
| 4,799,922 A | 1/1989 | Beer et al. | |
| 4,883,464 A | 11/1989 | Morifuki | |

(Continued)

FOREIGN PATENT DOCUMENTS

| | | |
|---|---|---|
| DE | 3916699 A1 | 12/1989 |
| EP | 0123269 | 10/1984 |

(Continued)

OTHER PUBLICATIONS

International Search Report; Oct. 11, 2010.

(Continued)

*Primary Examiner* — Theodore Stigell
*Assistant Examiner* — Gerald Landry, II
(74) *Attorney, Agent, or Firm* — Olson & Cepuritis, Ltd.

(57) ABSTRACT

The invention relates to a breast attachment, in particular a flexible insert for a breast pump or a nipple shield, wherein the insert or shield applies a positive massaging effect on a breast mimicking the natural stimulation of a baby breast feeding.

11 Claims, 3 Drawing Sheets

(56) References Cited

U.S. PATENT DOCUMENTS

| | | |
|---|---|---|
| 4,961,726 A | 10/1990 | Richter |
| 4,964,851 A | 10/1990 | Larsson |
| 5,007,899 A | 4/1991 | Larsson |
| 5,009,638 A | 4/1991 | Riedweg et al. |
| 5,049,126 A | 9/1991 | Larsson |
| 5,098,418 A | 3/1992 | Maitz et al. |
| 5,167,621 A | 12/1992 | Band et al. |
| 5,295,957 A | 3/1994 | Aida et al. |
| 5,358,476 A | 10/1994 | Wilson |
| 5,542,921 A | 8/1996 | Meyers et al. |
| 5,571,084 A | 11/1996 | Palmer |
| 5,676,525 A | 10/1997 | Berner et al. |
| 5,776,098 A | 7/1998 | Silver et al. |
| 5,782,837 A | 7/1998 | York |
| 5,810,772 A | 9/1998 | Niederberger |
| 5,885,246 A | 3/1999 | Ford |
| 5,902,267 A | 5/1999 | Medo |
| 5,941,847 A | 8/1999 | Huber et al. |
| 5,954,690 A | 9/1999 | Larsson |
| 6,042,560 A | 3/2000 | Niederberger |
| 6,045,529 A | 4/2000 | Nuesch |
| 6,090,065 A | 7/2000 | Giles |
| 6,110,141 A | 8/2000 | Nuesch |
| 6,149,395 A | 11/2000 | Richter |
| 6,257,847 B1 | 7/2001 | Silver et al. |
| 6,355,012 B1 | 3/2002 | Nuesch |
| 6,383,163 B1 | 5/2002 | Kelly et al. |
| 6,461,324 B1 | 10/2002 | Schlengsog |
| 6,481,986 B1 | 11/2002 | Silver et al. |
| 6,547,756 B1 | 4/2003 | Greter et al. |
| 6,579,258 B1 | 6/2003 | Atkin et al. |
| 6,676,631 B1 | 1/2004 | Greter |
| 6,699,213 B1 | 3/2004 | Annis et al. |
| 6,779,638 B2 | 8/2004 | Renz et al. |
| 6,808,517 B2 | 10/2004 | Greter et al. |
| 6,840,918 B1 | 1/2005 | Britto et al. |
| 6,921,379 B2 | 7/2005 | Greter et al. |
| 6,997,897 B1 | 2/2006 | Silver et al. |
| 7,008,400 B2 | 3/2006 | Silver et al. |
| 7,029,454 B2 | 4/2006 | Watanabe |
| 7,070,400 B2 | 7/2006 | Greter |
| 7,101,350 B2 | 9/2006 | Ytteborg |
| 7,150,346 B2 | 12/2006 | Renz et al. |
| 7,201,735 B2 | 4/2007 | Atkin et al. |
| 7,255,681 B1 | 8/2007 | Silver et al. |
| 7,354,418 B2 | 4/2008 | Lee et al. |
| 7,381,197 B2 | 6/2008 | Kelly et al. |
| 7,396,339 B2 | 7/2008 | Britto et al. |
| 2002/0072702 A1* | 6/2002 | Quay ............................ 604/74 |
| 2003/0139702 A1 | 7/2003 | Renz et al. |
| 2003/0149398 A1 | 8/2003 | Renz et al. |
| 2003/0236491 A1 | 12/2003 | McKendry et al. |
| 2004/0024351 A1* | 2/2004 | Greter et al. .................... 604/74 |
| 2004/0024352 A1 | 2/2004 | Renz et al. |
| 2004/0127845 A1 | 7/2004 | Renz et al. |
| 2004/0199107 A1 | 10/2004 | Nuesch |
| 2005/0085768 A1 | 4/2005 | Greter et al. |
| 2005/0154349 A1 | 7/2005 | Renz et al. |
| 2005/0165350 A1 | 7/2005 | Greter et al. |
| 2005/0256449 A1* | 11/2005 | Tashiro ............................ 604/74 |
| 2006/0030787 A1* | 2/2006 | Quay ............................ 600/573 |
| 2006/0052746 A1 | 3/2006 | Liao |
| 2007/0088250 A1* | 4/2007 | Silver et al. ...................... 604/74 |
| 2007/0161948 A1 | 7/2007 | Renz et al. |
| 2008/0033352 A1 | 2/2008 | Annis |
| 2008/0045887 A1 | 2/2008 | Larsson et al. |
| 2008/0195039 A1* | 8/2008 | Kataoka et al. .................. 604/74 |
| 2008/0208115 A1 | 8/2008 | Kliegman et al. |
| 2008/0255503 A1 | 10/2008 | Quackenbush et al. |
| 2009/0030368 A1* | 1/2009 | Silver .............................. 604/74 |
| 2010/0121265 A1 | 5/2010 | Bryan et al. |
| 2011/0098639 A1* | 4/2011 | Kirchner ........................ 604/74 |

FOREIGN PATENT DOCUMENTS

| | | |
|---|---|---|
| EP | 0909186 | 4/1994 |
| EP | 0727234 | 8/1996 |
| EP | 0733376 | 9/1996 |
| EP | 0846007 | 6/1998 |
| EP | 1068451 | 1/2001 |
| EP | 1107803 | 6/2001 |
| EP | 1221319 | 7/2002 |
| EP | 1263487 | 12/2002 |
| EP | 1468705 | 10/2004 |
| EP | 1490127 | 12/2004 |
| EP | 1498149 | 1/2005 |
| EP | 1502610 | 2/2005 |
| EP | 1593402 | 11/2005 |
| EP | 1923080 | 5/2008 |
| GB | 2106189 | 4/1983 |
| GB | 2399021 | 9/2004 |
| GB | 2399022 | 9/2004 |
| GB | 2418865 | 4/2006 |
| GB | 2420504 | 5/2006 |
| GB | 2434549 | 8/2007 |
| GB | 2435617 | 9/2007 |
| GB | 2435618 | 9/2007 |
| WO | 9000908 | 2/1990 |
| WO | 9705913 | 2/1997 |
| WO | 9822160 | 5/1998 |
| WO | 0066195 | 11/2000 |
| WO | 0147577 | 7/2001 |
| WO | 02010243 | 12/2002 |
| WO | 2004108184 | 12/2004 |
| WO | 2005016409 | 2/2005 |
| WO | 2007085032 | 8/2007 |
| WO | 2011007140 | 1/2011 |

OTHER PUBLICATIONS

Written Opinion of the International Searching Authority; Oct. 11, 2010.

US 6,306,115, 10/2001, Kelly et al. (withdrawn)

* cited by examiner

BREAST ATTACHMENT

CROSS-REFERENCE TO RELATED APPLICATIONS

This application is a National Stage Entry of PCT/GB2010/001345 filed on Jul. 14, 2010 and claims priority to GB0912229.2 filed on Jul. 14, 2009.

FIELD OF THE INVENTION

The invention relates to a breast attachment, in particular a flexible insert for a breast pump or a nipple shield, wherein the insert or shield applies a positive massaging effect on a breast mimicking the natural stimulation of a baby breast feeding.

BACKGROUND OF THE INVENTION

There are disadvantages associated with all known massaging breast pump inserts and shields.

The breast pump insert described in EP0727234 (Avent Limited) has recessed petals which rest against the breast and then move away from the breast when suction is applied due to the fact that the vacuum is directed to the space between the massaging insert and the rigid support horn. It is doubtful if the movement away from the breast actually provides any massaging effect.

U.S. Pat. No. 7,396,339 (The First Years Inc.) also describes a breast pump insert with recessed massaging petals, comprising regions within the massaging insert with thinned walls. However, the suction is directed via channels in the insert to the thinned regions in the space between the insert and the breast. As such, when suction is applied from the breast pump, the thinned regions move towards the breast and apply a massaging pressure. This could provide useful massage, but relies on the channels in the wall of the insert to direct suction to the recesses. However, the channels are small and will easily be blocked by the user's own breast.

Alternatively, US2004024352 (Playtex) has a massaging insert with a membrane, which again applies positive massaging force to the breast, but which utilises a build-up of pressure in the cavity between the massaging insert and the supporting horn. The breast pump described in US2004024352 either provides for no suction to the breast, which would otherwise encourage milk expression in the manner of most other known breast pumps, or it requires the breast pump to simultaneously apply suction to the breast and increased pressure to the massaging membrane. The latter would require a more complex breast pump than is desired.

It is well known that suction applied to the breast in short pulses provides the most efficient milk expression. As known in the art, applying suction to the breast stimulates milk expression by mimicking the action of a baby. The flexible regions of known breast pumps can assist milk expression by providing a small massaging effect. However, the flexible regions move by a pressure differential across a thinned region of material and the massaging pressure is therefore minimal because it relies on stretching the material, which requires a lot of energy.

Known nipple shields have a constant wall thickness and are either too rigid due to thick walls, which inhibits massage, or too flexible due to thin walls, which do not provide enough protection for the mother and risk damage to the shield.

SUMMARY OF THE INVENTION

Accordingly, the present invention provides a breast attachment that can be used as an insert in a breast pump or as a nipple shield to provide a positive massaging effect, which promotes milk expression. The attachment achieves this positive massaging effect by including at least one circumferential groove on the neck of the attachment and a cushioned outer rim. The circumferential grooves in the attachment of the invention provide weaknesses in the wall of the insert, which react to a decrease in pressure within the insert to collapse inwardly and significantly distort the attachment. The attachment shape change provides a much greater massaging pressure without needing to provide a lot of suction.

This is unlike the known art, where the massaging force is dependent on stretching the material and hence is directly proportional to the suction applied. In addition, the known breast pump inserts exert localised force, towards or away from the breast, acting approximately perpendicular from the breast, which is not representative of a baby's mouth. The shape change of the insert of the invention is much more representative of the action of a baby's mouth when feeding, so is likely to be more successful at causing milk expression. Specifically, the whole insert collapses and deforms, mimicking a baby's mouth as it goes from a wide "0" shape to a flattened shape.

When the insert is placed on the user's breast, the cushioned outer rim gives a comfortable feel due to the locating channel away from the surface of the insert which contacts the breast. Hence, when suction is applied and the user presses the pump onto her body, she cannot feel the hard outer rim of the rigid horn pressing through the flexible insert.

The invention also relates to a nipple shield that comprises the same circumferential grooves allowing the shield to collapse, as discussed above. Thus, the feeding baby can still apply a natural massaging effect and promote milk expression, even when the shield is in place. The shield also protects the mother's nipple.

BRIEF DESCRIPTION OF THE FIGURES

Embodiments of the invention will now be described by way of example with reference to the drawings of which.

DETAILED DESCRIPTION OF THE INVENTION

Figure 1:
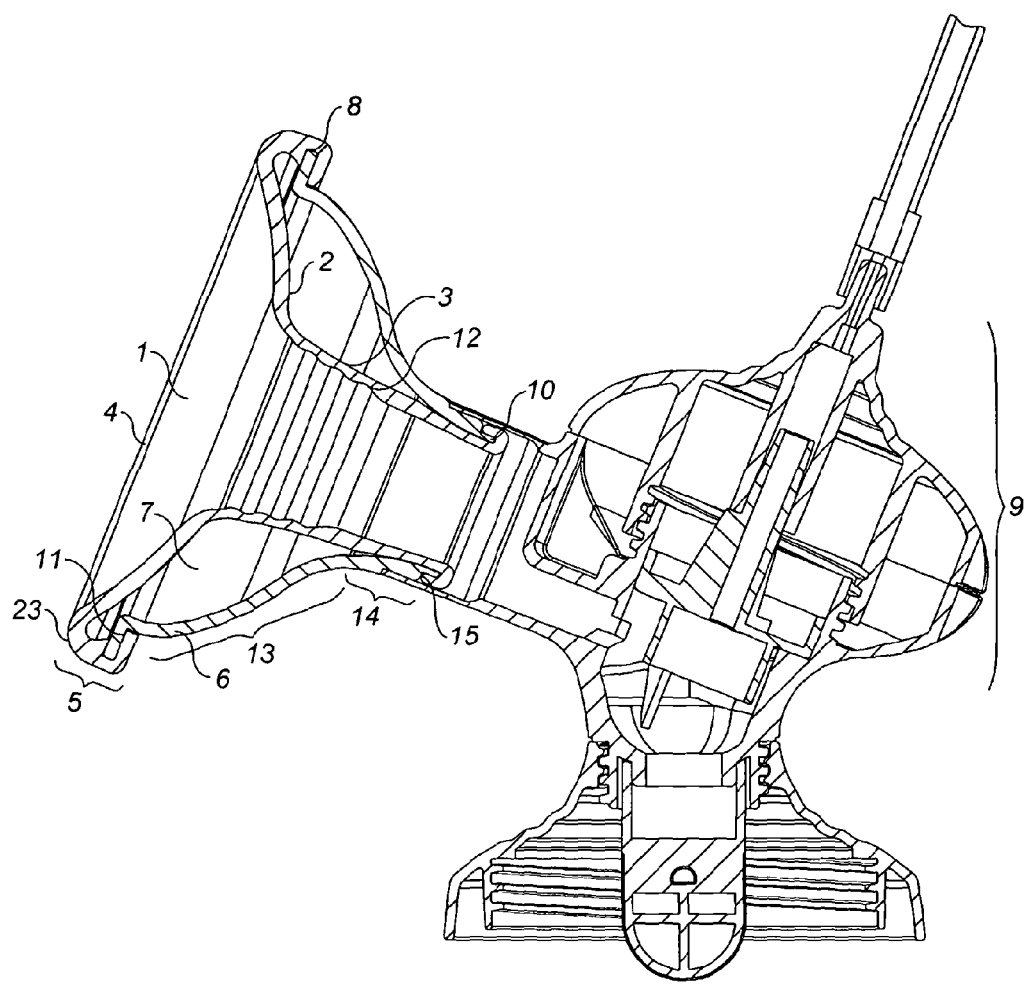
FIG. 1 shows a cross-section view of a breast pump insert (1), with a circular portion (2), attached to a head unit (9), which in turn is attached to a container and a pump lead.
Figure 2:
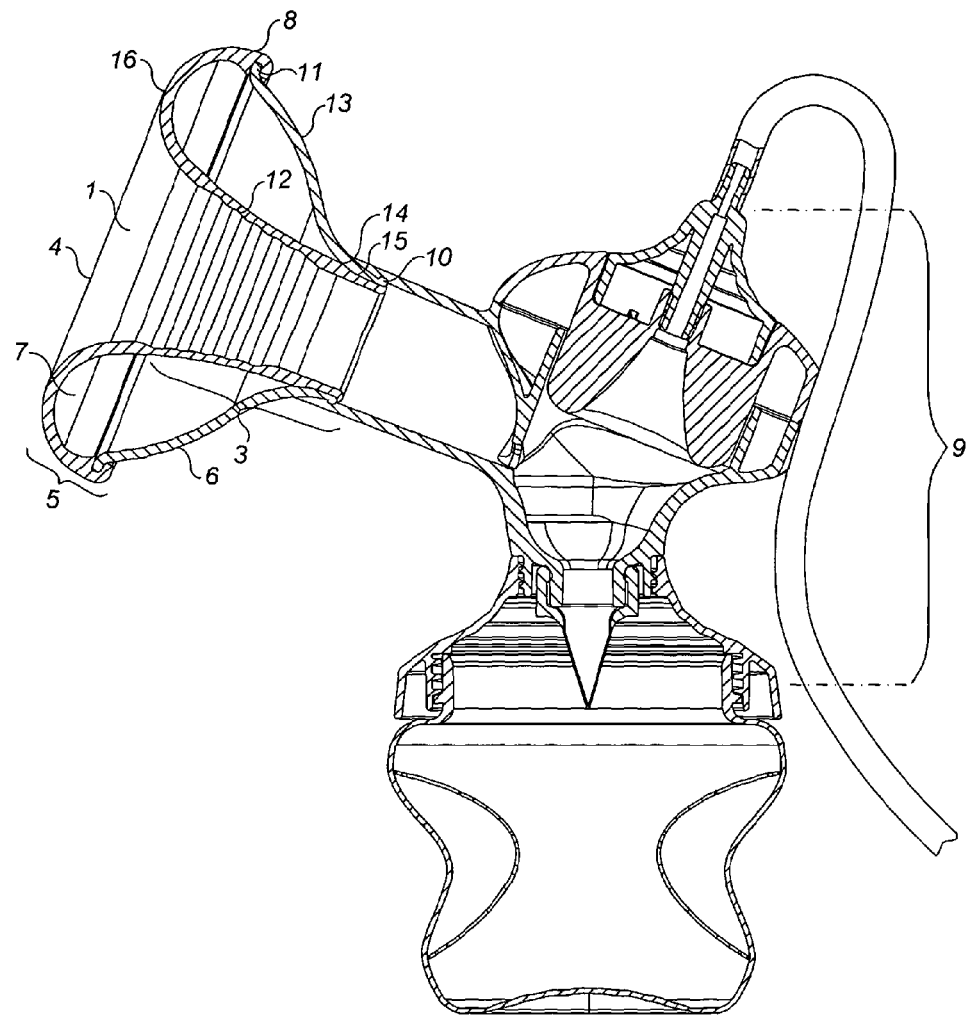
FIG. 2 shows a cross-section view of a breast pump insert (1) comprising a circular convex portion (16) in place of a circular cup portion.
Figure 3:
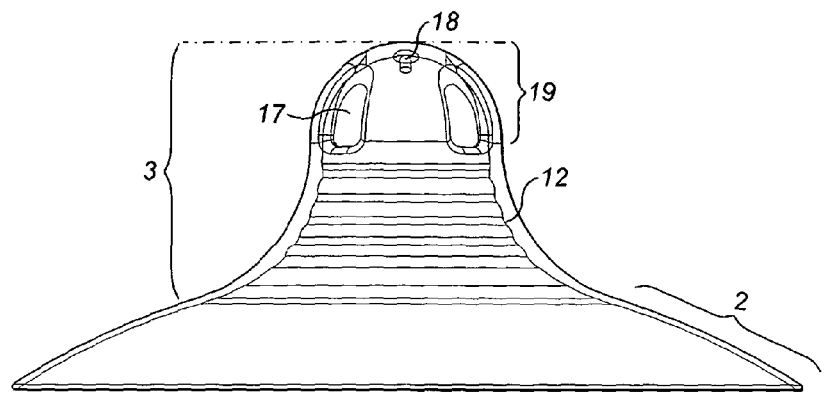
FIG. 3 shows a cross-section view of a nipple shield.
Figure 4:
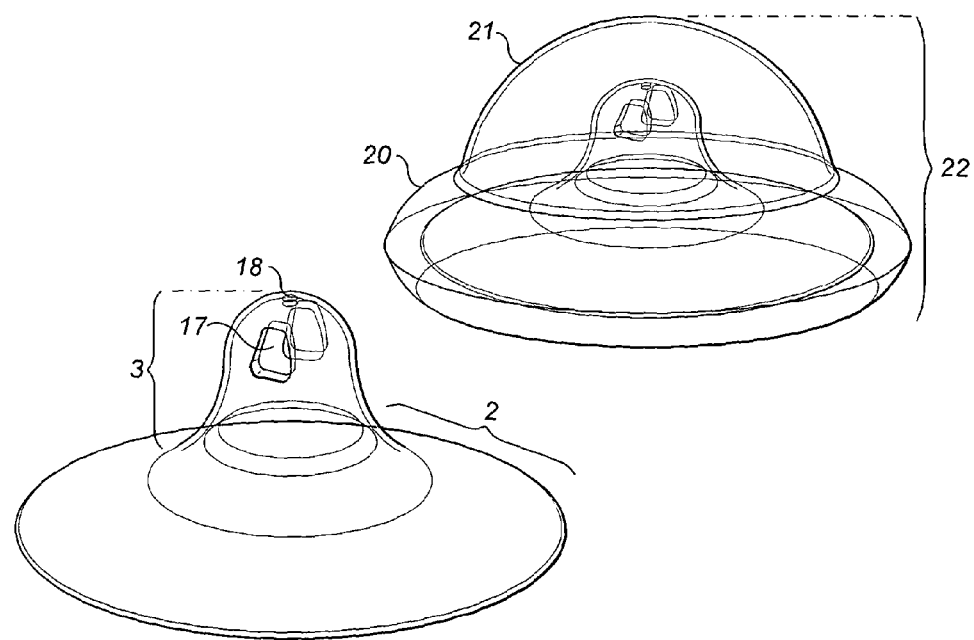
FIG. 4 shows an overview of a nipple shield.

The attachment can comprise a circular cup portion (2). At the base of the cup (2), the attachment also comprises a cylindrical neck (3) that extends from the cup portion (2) of the attachment (1). The attachment (1) is made of a flexible material.

The cylindrical portion (3) of the attachment (1) comprises at least one circumferential groove (12) on the inner surface. The grooves alternative with lands (i.e. ridges that result due to the grooves). Preferably the cylindrical portion (3) comprises two, three, four, five or six grooves. The grooves (12) can additionally or alternatively occur on the outer surface of the cylindrical portion (3). The attachment (1) does not include thinned regions around the circumferential grooves (12). The circumferential grooves (12) and lands provide the cylindrical portion (3) with an undulating cross section.

The attachment can be an insert for a breast pump. The circular portion (2) of the insert (1) has a shallow cup shape when it is not attached to any other components of the breast pump. The edge or rim (4) of the cup portion (2) folds back on itself to form a lip (5). By folding out and back on itself, this portion of the insert (1) also forms a rim (23) i.e. bulbous section that has a cushioning effect when in use.

The insert can also comprise a circular convex portion (16) in place of the circular cup portion. The convex portion (16) domes outward to provide a cushion against which the user can press. The convex portion (16) ensures that the breast cannot be pressed against the rim of the rigid horn.

When assembled for use, the insert (1) fits into a rigid horn (6), such that the entire of the inner surface of the rigid horn (6) is protected by the insert (1). The shape of the rigid horn (6) therefore corresponds generally to the shape of the flexible insert (1) i.e. the horn (6) is made up of a circular cup portion (13) with a cylindrical neck portion (14) extending from the base of the circular portion. The cup shape of the circular portion (13) of the horn (6) is significantly more pronounced than the cup-shape of the flexible insert (1) when the flexible insert (1) is not secured within the horn (6). The rigid horn (6) comprises a step (15) from the cup portion (13) to the cylindrical portion (14). When the rigid horn (6) is attached to a head unit (9), the entire cylindrical portion fits into a corresponding portion in the head unit A cavity (7) is formed between the flexible insert (1) and the rigid horn (6). The lip (5) of the flexible insert (1) at the edge of the circular portion (2) or circular convex portion (16) comprises a recess or channel (8) formed between a pointed ridge on the outer surface of the insert (1) and the outer edge of the lip (5). A corresponding portion of the rigid horn (6) fits into the recess or channel (8), so as to achieve a tight connection between the flexible insert (1) and the horn (6). Thus, the mouth of the insert (1) hooks onto the rigid horn (6).

The seal of the cavity (7) between the flexible insert (1) and the rigid horn (6) is broken by two small parallel flat-topped projections on the insert (1) that run perpendicular to the lip (5) at the edge of the circular portion. The projections can also run in any other direction relative to the lip provided the projections break the seal between the insert (I) and the horn (6). The projections may be any structure that juts out from the insert (1) e.g. a ridge, a bar or a formation. If the cavity (7) was sealed, deformation of the insert during use would change the volume of the cavity. This would affect the pressure and any change in pressure would provide resistance to the insert (1) deformation (thus inhibiting the amount of massaging provided by the insert). The two small flat-topped ridges provided on the insert (1) create an air passage around the outer rim of the horn (6) and ensures that the cavity (7) can maintain ambient pressure regardless of any volume deformations inside the cavity (7).

At the end of the cylindrical portion (3) of the insert (1) that attaches to a head unit (9), the insert portion also folds back on itself, to provide a channel or recess (10) into which the rigid horn (6) can tightly fit. Thus, the flexible insert (1) hooks onto the rigid horn (6) at both ends.

The portion of the rigid horn (6), which the cup portion of the insert (1) hooks onto is a flat rim (11) that fits into (or interacts with) the channel or recess of the insert (8). The other end of the rigid horn (6) that the cylindrical portion (3) of the insert (1) fits onto has a portion cut out to leave a section of cylindrical rigid horn that is thinner than the remainder of the horn and that fits into (or interacts with) the recess or channel (10) provided by the insert (1).

When the flexible insert (1) is attached to the rigid horn (6), the flexible insert (1) is stretched causing the cup shape of the insert (1) to become more pronounced and correspond generally to the shape of a breast, such that the insert (I) can be placed on a breast.

The combined structure of the insert (1) and rigid horn (6) attaches to a head unit (9) i.e. the main body of the pump) at the end of the cylindrical portion (3).

The head unit (9) can be attached to a manual pump or an electrical pump. A suitable electric pump is a diaphragm pump.

When in use the head unit (9) is also connected to a container in which the milk is collected. The head unit (9) can comprise an internal thread for screwing the unit onto a container. The unit can also comprise a one way valve at the portion of the unit that attaches to the container, such that when a container is attached, milk passes through the unit and the valve into the container. The one way valve may be a duck-bill valve or flap valve as known in the art.

When in use, suction is applied to the breast and the flexible insert by a pump causing the flexible insert to collapse along the circumferential grooves. This causes the cylindrical neck (3) of the insert (I) to collapse and distort, going from a circular cross-section to a flattened oval cross-section. This change in shape provides a massaging pressure on the breast, which stimulates milk production.

After the suction pulse ends and the pump bleeds air back into the unit and the flexible insert (1) returns to the original shape. Any milk that is expressed during the suction cycle will pass down the neck of the insert (1) into the unit body (9) and subsequently into a storage container via a one-way valve.

The two flat-topped projections on the insert (1) ensure that deformation of the insert occurs with minimal resistance because the cavity (7) between the flexible insert (1) and the rigid horn (6) is not sealed from the ambient atmosphere.

The flexible insert (1) can be made from silicone rubber, while the horn (6) and head unit (9) of the pump can be made from a rigid plastic such as polypropylene.

The attachment can also be a nipple shield. When the attachment is a nipple shield the cylindrical neck terminates with a domed portion (19), shaped to receive a nipple.

The dome shaped portion (19) of the shield comprises at least one cut-out portion (17). The cut-out portions can represent substantially a fifth, a quarter, a third or more of the total domed portion. The domed portion can additionally comprise smaller holes (18) in the tip of the domed portion.

The cup shaped portion of the nipple shield is a wide, flat region that can be made of thin material and can seal to a breast The cylindrical portion (3) and the domed portion (19) can be made from thicker material.

The nipple shield can be made from silicone rubber.

When in use the nipple shield is placed on a breast and a baby sucks the cylindrical portion (3). As the baby feeds, the circumferential grooves (12) in the cylindrical portion (3) cause the shield to collapse and thereby exerting a natural massaging effect on the breast, promoting milk release.

The baby may also apply a massaging action caused by changing the shape of its mouth from an "0" to a flatter shape. The circumferential grooves (12) thereby ensure that the nipple shield can collapse easily and transmit the natural massaging action to the breast with minimal interference. In other words, if the shield does not collapse it will resist the massaging force from the baby's feeding action. This is undesirable as the nipple shield will inhibit the natural feeding action and reduce stimulation of the breast which may, ultimately, cause the mother's milk supply to decrease.

The cut-out portions allow release of a substantial amount of milk into the baby's mouth. In addition, the cut-out portions can mean that the baby can feel the mother's nipple.

When not in use the shield can be stored and protected by a casing. The casing (22) comprises a first cup shaped portion (20) with a second dome shaped portion (21) to accommodate the nipple portion of the shield.

The invention claimed is:

1. A flexible breast attachment comprising:
   a cup portion constructed and arranged to receive and sealingly engage a human breast;
   a cylindrical portion, extending from the cup portion having an inner surface and an outer surface;
   at least one circumferential groove disposed on the inner surface for enabling the cylindrical portion to collapse along the at least one circumferential groove, whereby the cylindrical portion can move from an uncollapsed state having a generally circular cross-section to a collapsed state having a generally flattened oval cross-section so as to exert a massaging effect on the breast.

2. The flexible breast attachment of claim 1, wherein the cylindrical portion terminates in a domed portion into which the nipple of the breast can be received.

3. The flexible breast attachment of claim 2, wherein the domed portion comprises cut-out regions.

4. The flexible breast attachment of claim 1, wherein the cylindrical portion is adapted to communicate with a suction pressure source for causing the cylindrical portion to collapse along the one circumferential groove.

5. The flexible breast attachment of claim 1 further comprising a first lip portion disposed at a distal end of the cup portion for providing a cushioning effect with the breast, and a second lip portion disposed at a distal end of the cylindrical portion.

6. A breast pump assembly comprising:
   a rigid horn having a circular cup portion adapted for receiving and sealingly engaging with a breast and a cylindrical neck portion extending from the circular cup portion, the cylindrical neck portion having an inner surface and an outer surface;
   a breast pump insert secured with the rigid horn and having at least one circumferential groove disposed on the inner surface, wherein the breast pump insert is adapted for collapsing along the at least one circumferential groove;
   a suction pressure source in communication with the breast pump insert for exerting a suction pressure to enable the cylindrical portion to collapse along the at least one circumferential groove, whereby the cylindrical portion can move from an uncollapsed state having a generally circular cross-section to a collapsed state having a generally flattened oval cross-section so as to exert a massaging effect on the breast to express liquid therefrom; and
   a container for collecting liquid expressed from the breast.

7. The breast pump assembly of claim 6, wherein the suction pressure source is a diaphragm pump for causing the cylindrical portion to collapse along the one circumferential groove.

8. The breast pump assembly of claim 6, wherein the breast pump insert comprises at least one projection arranged and constructed to space the rigid horn and the breast pump insert for providing an air passage around an outer rim of the rigid horn.

9. The breast pump assembly of claim 6, wherein the breast pump insert further comprises lip portions disposed at opposite end portions of the breast pump insert, wherein the breast pump insert is secured proximate an inner surface of the rigid horn by engagement between the lip portions of the breast pump insert and corresponding engagement portions of the rigid horn.

10. A method of expressing milk from a human breast using a rigid horn, a breast pump insert secured to the rigid horn and having at least one circumferential groove and adapted for collapsing along the at least one circumferential groove, a suction pressure source in communication with the breast pump insert, and a container for collecting expressed milk from the human breast, the method comprising:
    placing the rigid horn in sealing engagement with the human breast,
    applying a suction pressure to the breast pump insert for enabling the cylindrical portion to collapse along the at least one circumferential groove, whereby the cylindrical portion can move from an uncollapsed state having a generally circular cross-section to a collapsed state having a generally flattened oval cross-section so as to exert a massaging effect on the breast causing expression of milk; and
    collecting the expressed milk in the container.

11. The breast pump assembly of claim 6 further comprising a cavity between the rigid horn and the breast pump insert.

* * * * *